United States Patent [19]

Shaw et al.

[11] Patent Number: 5,678,572
[45] Date of Patent: Oct. 21, 1997

[54] CAVITY EXPANDING DEVICE FOR LAPAROSCOPIC SURGERY

[76] Inventors: Dein Shaw, 5F., No. 5-1, Alley 7, Lane 155, Kuang Fu Rd., Sec. 2, Hsing Chu; Ming-Te Huang, 3F., No. 318-1, Fu Hsing South Rd., Sec. 1, Taipei, both of Taiwan

[21] Appl. No.: 371,971

[22] Filed: Jan. 12, 1995

[51] Int. Cl.⁶ ............................ A61B 17/02
[52] U.S. Cl. ............................ 128/899; 606/198
[58] Field of Search ............... 128/899; 606/191, 606/192, 198; 600/201, 203, 204, 205–208, 210, 211, 214, 215, 219

[56] References Cited

U.S. PATENT DOCUMENTS

| | | | |
|---|---|---|---|
| 3,517,128 | 6/1970 | Hines | 606/198 |
| 5,275,610 | 1/1994 | Eberbach | 606/198 |
| 5,318,586 | 6/1994 | Ereren | 606/198 X |
| 5,325,848 | 7/1994 | Adams et al. | 600/204 X |
| 5,351,697 | 10/1994 | Mayzels et al. | 600/214 |
| 5,454,365 | 10/1995 | Bonutti | 600/204 |
| 5,468,248 | 11/1995 | Chin et al. | 606/192 |

*Primary Examiner*—Lee S. Cohen
*Assistant Examiner*—Samuel Gilbert
*Attorney, Agent, or Firm*—Bacon & Thomas

[57] ABSTRACT

An auxiliary cavity expanding device for an operation which may prop up a body portion for laparoscopic surgery in order to make space for the performance of the operation includes a plurality of stays and a stay sleeve. The stays are secured to a stay end tube and an end of each stay is provided with a stay pusher to shift the stays relative to the stay sleeve. This shifting causes bending of the stays and expanding of the cavity for the operation. After expansion, the stays can be secured in a desired position by screws which secure the stays relative to the stay sleeve.

1 Claim, 4 Drawing Sheets

CAVITY EXPANDING DEVICE FOR LAPAROSCOPIC SURGERY

BACKGROUND OF THE INVENTION

1. Field of the Invention

The present invention relates to a device for laparoscopic-surgery, and particularly to a cavity expanding device including a hollow cylinder and some soft thin strips, which is adapted to be inserted into an operation location during a surgery and wherein the thin strips are pushed which causes them to bend so that the operation location is expanded to give a wider space in order to facilitate the operation.

2. Discussion of the Prior Art

In order to make adequate space for an operation, a conventional laparoscopic-surgery often has used carbon dioxide to pressurize the abdominal cavity to make it expanded in order to facilitate the operation.

The aforesaid way of distending the abdominal wall to produce a safety space above the patient's abdominal organs for operation often has associated therewith a problem relating to either the infiltration of pressurized carbon dioxide into the blood or air leakage. Some patents have presented some improvements in this art in an attempt to solve this problem, such as U.S. Pat. No. 5,318,012 wherein a device is disclosed for insertion in the body and for pulling up on an abdominal wall through the application of an external force to produce a safety space above the patient's abdominal organs to avoid the need of blocking in air. However, the defect of such an arrangement lies in the abdominal wall depending on an external force for pulling it up since a large stress is placed on this area and therefore damage can occur to the area such that the wound is actually expanded.

Often, some internal organs or tissues are disposed under other organs when a patent is lying on his or her back. In order to lift or displace the overlying organs in order to operate on the underlying organs, a variety of retractors have been invented (see U.S. Pat. Nos. 5,152,279, 5,1781,133 and 5,267,554) which enable one to lift an overlying organ with some type of supporter. In accordance with these arrangements, the whole operation is restricted by the length of the supporters so it has caused a problem in the medical area that an excellent environment for operation cannot be achieved.

SUMMARY OF THE INVENTION

An object of the present invention is to provide a prop-up or cavity expansion device that may enlarge an area for an operation such as through the use of long thin strips which are bent to separate the organs in order to made a wider space to facilitate the operation.

Another object of the present invention is to provide a hollow cylinder that may be used to extend a laparoscope into an operation area and may provide a passage for a scalpel, clip, etc. extending into the body for treatment.

These and other objects and advantages of the present invention will become apparent to those skilled in art after considering the following detailed description of preferred embodiments when taken in conjunction with the accompanying drawings.

DETAILED DESCRIPTION OF THE PREFERRED EMBODIMENTS

Figure 1:
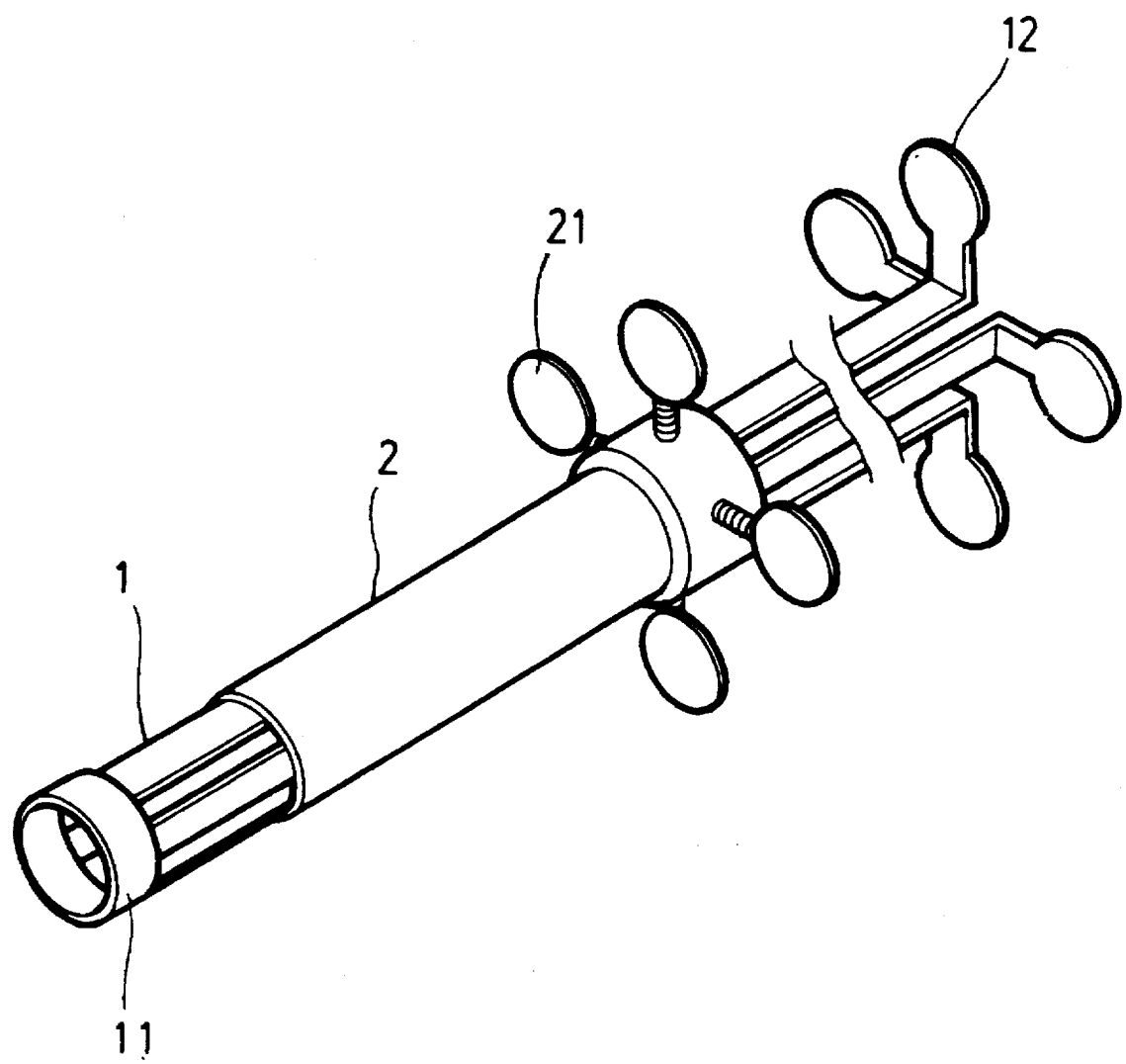
FIG. 1 is a schematic perspective view of the cavity expanding device according to a first embodiment of the invention.
Figure 2:
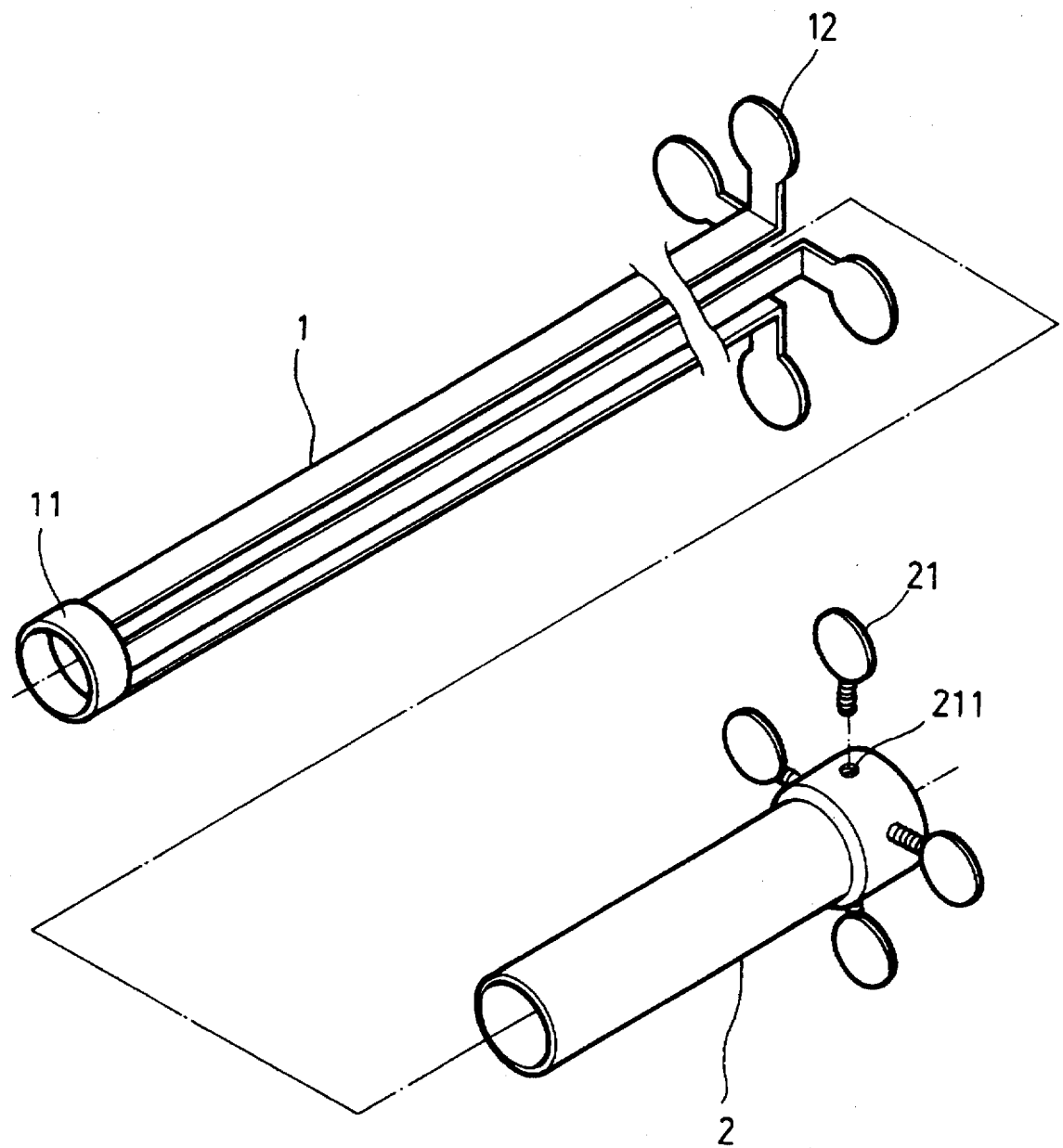
FIG. 2 is an exploded view of the device of FIG. 1.

Referring initially to FIGS. 1 and 2, the cavity expanding device of the invention is shown to include a plurality of expansion members or stays 1 (not restricted by length, number and degree of distribution) which are connected by means of a stay end tube 11. An end of each of the stays 1, remote from stay end tube 11, is provided with a respective stay pusher 12.

The stay sleeve 2 constitutes a hollow through tube through which each stay 1 passes. Stay sleeve 2 may move relative to stays 1. One end of stay sleeve 2 has a plurality of threaded holes 211 which receive screws 21 to individually retain each stay 1 so as to prevent relative movement between stays 1 and stay sleeve 2 when the screws 21 are tightened.

Figure 3A:
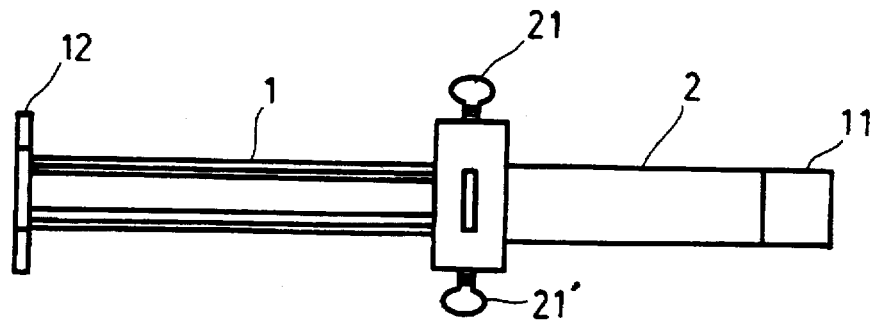
FIG. 3a is a side view of the device in a first position.
Figure 3B:
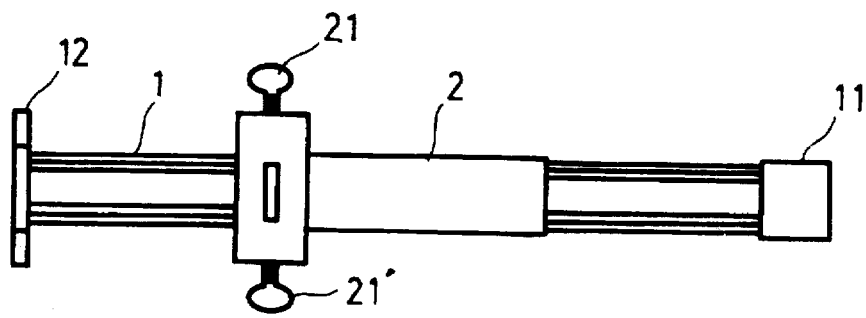
FIG. 3b is a side view of the device in a second position.
Figure 3C:
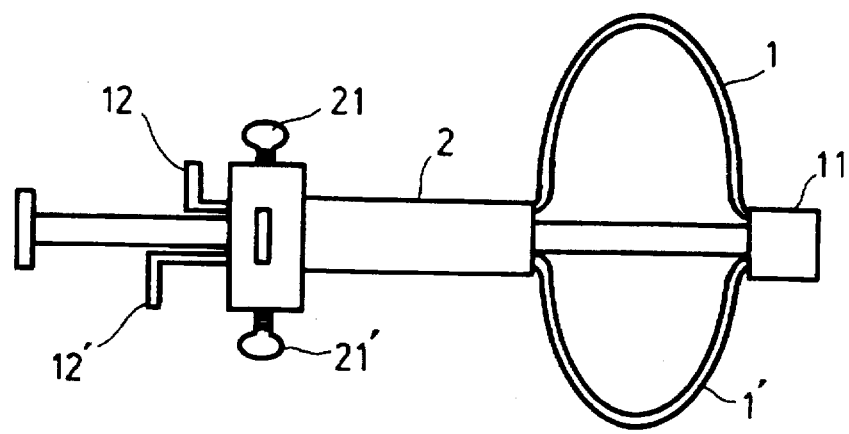
FIG. 3c is a side view of the device in a third position.
Figure 3D:
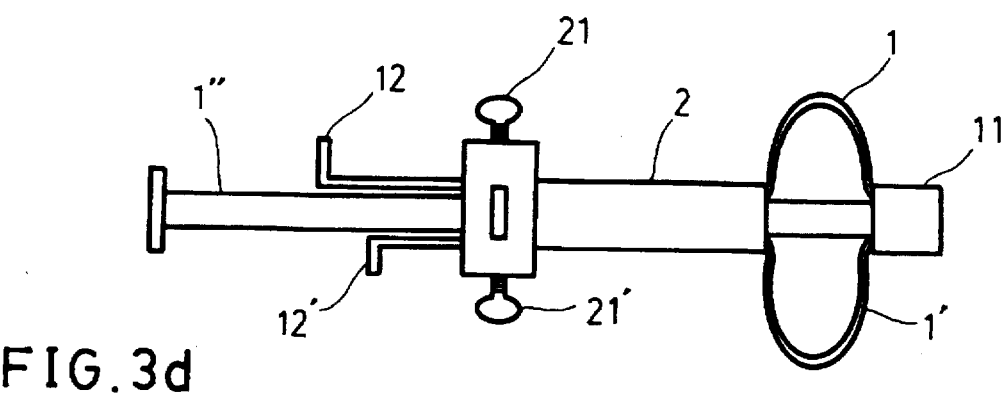
FIG. 3d is a side view of the device in a fourth position.

Referring to FIG. 3a stay sleeve 2 may be pushed forward to contact stay end tube 11. In this condition, stay sleeve 2 can be placed into a portion of the body during an operation. Stay sleeve 2 may then be pulled backward a desired mount depending on the area to be expanded as represented in FIG. 3b. It is also possible to keep stay sleeve 2 still while pushing stay end tube 11 in order to reach the appropriate position. Stays 1, 1' can then be pushed by stay pushers 12, 12' which causes stays 1, 1' to move toward stay end tube 11 which forces stays 1, 1' to get bent, thereby causing the operation area or cavity to expand (FIG. 3c). Note that each stay is separately pushed forward to identical or different lengths so that the stays may prop open in accordance with the desired shape of the cavity to be formed. With screws 21, 21', stays 1, 1' can be secured to the desired position. In addition, stays 1, 1' may be initially fixed while enabling stay 1" to be pulled backward to cause stays 1, 1' to expand. It is noted that, while pushing the stay pushers 12 to bend the stay 1, stay end tube 11 should be kept in a fixed position and resist the pushing force. To do so, at least one stay 1 is secured, by the tightening screw without bending before the other stay pushers 12 are acted upon.

Figure 4A:
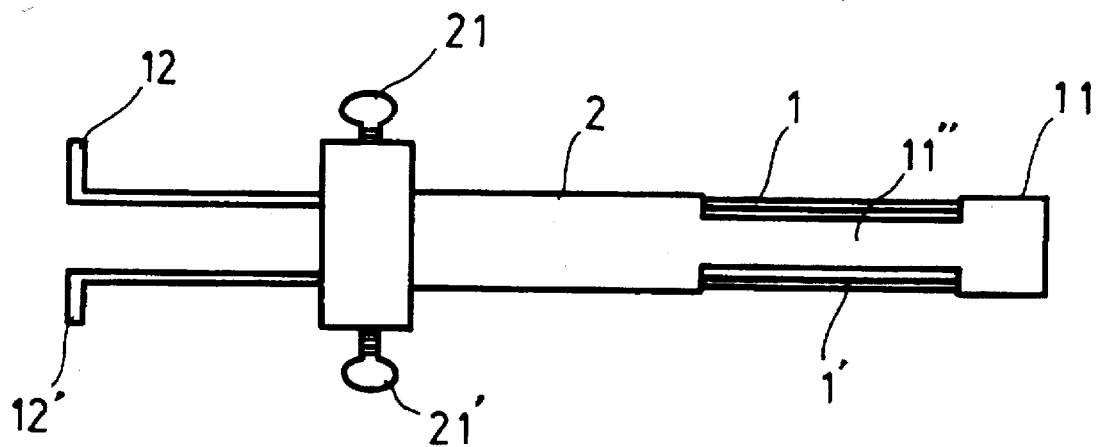
FIG. 4a is a side view of the device according to a second embodiment of the invention.
Figure 4B:
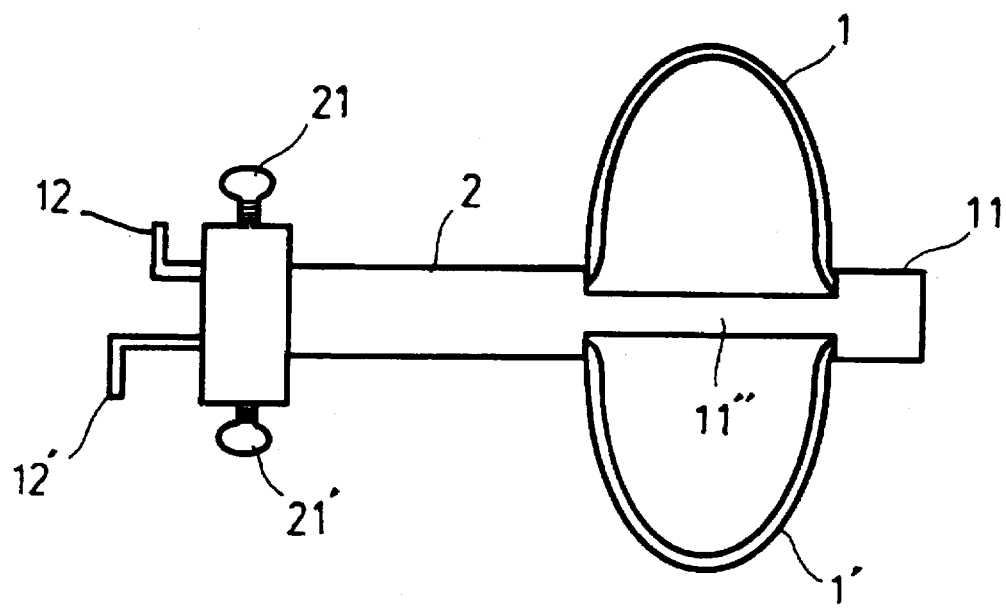
FIG. 4b is a side view of the device of FIG. 4a but in an expanded position.

Referring to FIGS. 4a and 4b, stay end tube 11 can be directly connected with stay sleeve 2 by means of flat strips 11". Shifting stay pushers 12, 12' relative to stay sleeve 2 will enable stays 1, 1' to expand up by bending to assume the shape of the abdomen or cavity as desired. Thereafter, stays 1, 1' can be secured by tightening screws 21, 21'.

Stays according to the invention may also be replaced by a soft, hollow tube. Upon expanding and propping up the body portion for the operation, pressure fluid (e.g. air, saline) may be supplied therein to cause the tube to get hard while increasing the cavity expansion strength on the body portion for the operation.

We claim:

1. A cavity expansion device for use during laparoscopic surgery comprising:

a plurality of flexible expansion members each including first and second end portions;

means for interconnecting the second end portion of each of said expansion members;

a sleeve member through which said expansion members slidably extend, wherein an internal passage is formed within said sleeve member to receive a laparoscope; and means for individually, fixedly securing said expansion members to said sleeve member, wherein said expansion members can be selectively, individually shifted relative to said sleeve member through force applied to a respective said first end portion to cause flexing of the second end portions of said expansion members, whereby said expansion members can be flexed varying amounts relative to each other and maintained in varying flexed positions by said securing means.

* * * * *